US010981971B2

(12) United States Patent
Mai

(10) Patent No.: US 10,981,971 B2
(45) Date of Patent: Apr. 20, 2021

(54) FUSION PROTEIN FOR TREATING ALZHEIMER'S DISEASE

(71) Applicant: SHENZHEN MAIDIKE BIOTECHNOLOGY CO., LTD., Guangdong (CN)

(72) Inventor: Junbo Mai, Guangdong (CN)

(73) Assignee: SHENZHEN PREPHARM BIOMEDICAL TECH CO., LTD., Shenzhen (CN)

( * ) Notice: Subject to any disclaimer, the term of this patent is extended or adjusted under 35 U.S.C. 154(b) by 0 days.

(21) Appl. No.: 16/304,606

(22) PCT Filed: Jul. 13, 2017

(86) PCT No.: PCT/CN2017/092850
§ 371 (c)(1),
(2) Date: Nov. 26, 2018

(87) PCT Pub. No.: WO2017/202394
PCT Pub. Date: Nov. 30, 2017

(65) Prior Publication Data

US 2019/0300596 A1 Oct. 3, 2019

(30) Foreign Application Priority Data

May 26, 2016 (CN) ......................... 201610365327.8

(51) Int. Cl.

| | |
|---|---|
| ***C07K 14/705*** | (2006.01) |
| ***C07K 14/54*** | (2006.01) |
| ***A61K 38/20*** | (2006.01) |
| ***A61K 38/18*** | (2006.01) |
| ***C07K 19/00*** | (2006.01) |
| ***A61K 38/00*** | (2006.01) |
| ***A61P 25/28*** | (2006.01) |
| ***C12N 15/85*** | (2006.01) |
| ***C12N 15/66*** | (2006.01) |

(52) U.S. Cl.
CPC ........ *C07K 14/70578* (2013.01); *A61K 38/18* (2013.01); *A61K 38/20* (2013.01); *A61P 25/28* (2018.01); *C07K 14/54* (2013.01); *C07K 19/00* (2013.01); *C12N 15/66* (2013.01); *C12N 15/85* (2013.01); *A61K 38/00* (2013.01); *C07K 2319/32* (2013.01)

(58) Field of Classification Search
CPC .. C07K 14/70578; C07K 19/00; C07K 14/54; C07K 2319/32; C07K 14/70571; C07K 2319/00; C07K 14/71; A61K 38/20; A61K 38/18; A61K 38/00; C12N 15/85; C12N 15/66; C12N 2800/107; A61P 25/28
See application file for complete search history.

(56) References Cited

FOREIGN PATENT DOCUMENTS

| | | | |
|---|---|---|---|
| CN | 101157730 A | | 4/2008 |
| CN | 101775072 A | | 7/2010 |
| CN | 102233128 A | * | 11/2011 |
| CN | 102233128 A | | 11/2011 |
| CN | 102586313 A | | 7/2012 |
| CN | 104302326 A | | 1/2015 |
| CN | 106046171 A | | 10/2016 |
| WO | 96/12955 | | 5/1996 |
| WO | 2004/000877 A2 | | 12/2003 |
| WO | WO-2015042521 A1 | * | 3/2015 |

OTHER PUBLICATIONS

"Interleukin 33 [*Homo sapiens*]" Gen Bank accession No. AAH47085. 1. retrieved Aug. 1, 2019 from https://www.ncbi.nlm.nih.gov/protein/AAH47085.*
Vickers, JC. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
"Cloning a C-terminal GFP fusion: is it okay that I still have the start codon for both my gene and the GFP?" ResearchGate Web Site, retrieved from https://www.researchgate.net/post/Cloning_a_C-terminal_GFP_fusion_is_it_okay_that_I_still_have_the_start_codon_for_both_my_gene_and_the_GFP on Feb. 7, 2020.*
Chapuis, J. et al., "Transcriptomic and genetic studies identifyh IL-33 as a candidate gene for Alzheimer's disease", Mol. Psychiatry, 14(11): 1004-1016 (2009).

(Continued)

*Primary Examiner* — Gregory S Emch
(74) *Attorney, Agent, or Firm* — Yu Gang

(57) ABSTRACT

A fusion protein used for preventing and treating Alzheimer's disease, a preparation method therefor, and an application thereof. The fusion protein comprises the extracellular domain of human p75NTR human IL-33 and a linker peptide respectively connected to the carboxyl terminus of the p75NTR-ECD and the amino terminus of the human IL-33. The amino acid sequence of the p75NTR-ECD is as shown in SEQ ID NO: 1, and the nucleotide sequence is as shown in SEQ ID NO: 2. The amino acid sequence of the human IL-33 is as shown in SEQ ID NO: 3, and the nucleotide sequence is as shown in SEQ ID NO. 4. The invention overcomes the defects of the p75NTR-ECD or a fusion protein p75NTR-ECD-FC), for preventing and treating Alzheimer's disease. In addition, the functions of the IL-33 and the p75NTR-ECD are combined together, and the biological activity for preventing and treating Alzheimer's disease is significantly increased.

1 Claim, 4 Drawing Sheets

Specification includes a Sequence Listing.

(56) References Cited

OTHER PUBLICATIONS

Fu, Amy K. Y. et al., "IL-33 ameliorates Alzheimer's disease-like pathology and cognitive decline", PNAS, E2705-E2713 (2016).
Zhou, Xin-Fu et al., "The p75NTR extracellular domain", Prion, 5(3): 161-163 (2011).
Strausberg, R.L. et al., "Interleukin 33 [*Homo sapiens*]", GenBank: AAH47085.1, Dec. 2, 2006, pp. 1-2.
Li,Jianfang et al., "Design of Linker Peptides and Its Application in Fusion Protein", Journal of Food Science and Biotechnology, 2015, 34 (11), Nov. 15, 2015, pp. 1121-1127.

* cited by examiner

SEQUENCE LISTING

<160> NUMBER OF SEQ ID NOS: 27

<210> SEQ ID NO 1

```
<211> LENGTH: 250
<212> TYPE: PRT
<213> ORGANISM: Homo sapiens

<400> SEQUENCE: 1

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn
                245                 250


<210> SEQ ID NO 2
<211> LENGTH: 750
<212> TYPE: DNA
<213> ORGANISM: Artificial Sequence
<220> FEATURE:
<223> OTHER INFORMATION: p75NTR-ECD which is the extracellular domain of
      human p75NTR

<400> SEQUENCE: 2

atgggtgcag gggcgaccgg tagggcgatg gatgggcccc ggctgttact gcttttgcta      60

ttaggcgttt ctcttggcgg ggcgaaggag gcgtgcccga cagggctcta cacgcacagc     120

ggggagtgct gtaaggcatg taacttgggc gaaggcgtgg cacaaccctg tggcgccaac     180

cagactgtat gcgagccctg tctagattct gtgactttct cggatgtagt ctcggctaca     240

gaaccctgca agccttgtac cgaatgcgta gggcttcagt cgatgtcggc tccgtgtgtc     300

gaggctgacg acgcggtgtg tcgctgtgcc tacggctact accaagacga aacaacggga     360

cgctgcgagg cttgtcgcgt atgtgaagct gggagcggcc ttgtgttttc ttgtcaagat     420
```

-continued

```
aagcaaaaca cagtttgtga agaatgcccc gacgggactt acagcgacga ggcaaatcat    480

gtggaccctt gtcttccgtg taccgtttgc gaggacactg agcgacaact aagggaatgc    540

accaggtggg cagacgccga atgcgaagaa ataccgggca gatggataac acgctccacg    600

ccgcctgagg gtagcgattc cacagctcca tccacacagg agcctgaagc tccaccggaa    660

caggatttaa tcgcttctac cgtggccgga gtggtcacaa cagtcatggg gtcgtcacaa    720

cctgtagtaa cacgagggac gacagacaac                                      750


<210> SEQ ID NO 3
<211> LENGTH: 269
<212> TYPE: PRT
<213> ORGANISM: Homo sapiens

<400> SEQUENCE: 3

Lys Pro Lys Met Lys Tyr Ser Thr Asn Lys Ile Ser Thr Ala Lys Trp
1               5                   10                  15

Lys Asn Thr Ala Ser Lys Ala Leu Cys Phe Lys Leu Gly Lys Ser Gln
            20                  25                  30

Gln Lys Ala Lys Glu Val Cys Pro Met Tyr Phe Met Lys Leu Arg Ser
        35                  40                  45

Gly Leu Met Ile Lys Lys Glu Ala Cys Tyr Phe Arg Arg Glu Thr Thr
    50                  55                  60

Lys Arg Pro Ser Leu Lys Thr Gly Arg Lys His Lys Arg His Leu Val
65                  70                  75                  80

Leu Ala Ala Cys Gln Gln Gln Ser Thr Val Glu Cys Phe Ala Phe Gly
                85                  90                  95

Ile Ser Gly Val Gln Lys Tyr Thr Arg Ala Leu His Asp Ser Ser Ile
            100                 105                 110

Thr Gly Ile Ser Pro Ile Thr Glu Tyr Leu Ala Ser Leu Ser Thr Tyr
        115                 120                 125

Asn Asp Gln Ser Ile Thr Phe Ala Leu Glu Asp Glu Ser Tyr Glu Ile
    130                 135                 140

Tyr Val Glu Asp Leu Lys Lys Asp Glu Lys Lys Asp Lys Val Leu Leu
145                 150                 155                 160

Ser Tyr Tyr Glu Ser Gln His Pro Ser Asn Glu Ser Gly Asp Gly Val
                165                 170                 175

Asp Gly Lys Met Leu Met Val Thr Leu Ser Pro Thr Lys Asp Phe Trp
            180                 185                 190

Leu His Ala Asn Asn Lys Glu His Ser Val Glu Leu His Lys Cys Glu
        195                 200                 205

Lys Pro Leu Pro Asp Gln Ala Phe Phe Val Leu His Asn Met His Ser
    210                 215                 220

Asn Cys Val Ser Phe Glu Cys Lys Thr Asp Pro Gly Val Phe Ile Gly
225                 230                 235                 240

Val Lys Asp Asn His Leu Ala Leu Ile Lys Val Asp Ser Ser Glu Asn
                245                 250                 255

Leu Cys Thr Glu Asn Ile Leu Phe Lys Leu Ser Glu Thr
            260                 265


<210> SEQ ID NO 4
<211> LENGTH: 810
<212> TYPE: DNA
<213> ORGANISM: Artificial Sequence
<220> FEATURE:
<223> OTHER INFORMATION: Human IL-33
```

<400> SEQUENCE: 4

```
aaacctaaaa tgaaatattc gactaacaaa attagtaccg cgaaatggaa aaacaccgcg     60
tcaaaggcgc tttgctttaa gcttggcaag tcgcagcaga aagcgaaaga agtctgtcca    120
atgtatttca tgaaactgcg gtcggggtta atgattaaga aagaggcatg ttattttaga    180
cgcgagacca ctaagcgccc ctctctcaag acaggtcgta aacacaaacg tcacctggtg    240
ctagccgctt gtcagcagca atctactgtc gagtgttttg ctttcgggat cagcggggtg    300
caaaagtaca caagggcgct gcatgacagt agcattactg gtataagtcc aataacagag    360
tatcttgctt cactcagtac ttataacgat cagtccataa cgttcgcact ggaggacgaa    420
tcatacgaga tctacgtaga agatctcaag aaagacgaaa aaaaagataa agtcttactg    480
tcgtattatg aatctcagca cccttcgaac gagagcggcg atggagttga cgggaagatg    540
ctaatggtta ctttatcccc taccaaggat ttttggcttc atgccaataa taaagagcac    600
tccgttgagc tccataaatg cgaaaaaccc ctcccggatc aggcgttttt tgttctccac    660
aatatgcata gtaattgcgt ctcattcgag tgtaaaacgg acccaggtgt ttttatcggt    720
gtgaaggata accacctggc tctgattaag gtagactcaa gtgaaaactt gtgcacggaa    780
aacatacttt ttaagttatc ggagacataa                                     810
```

<210> SEQ ID NO 5
<211> LENGTH: 15
<212> TYPE: PRT
<213> ORGANISM: Artificial Sequence
<220> FEATURE:
<223> OTHER INFORMATION: Linker

<400> SEQUENCE: 5

```
Gly Gly Gly Gly Ser Gly Gly Gly Gly Ser Gly Gly Gly Gly Ser
1               5                   10                  15
```

<210> SEQ ID NO 6
<211> LENGTH: 45
<212> TYPE: DNA
<213> ORGANISM: Artificial Sequence
<220> FEATURE:
<223> OTHER INFORMATION: Linker

<400> SEQUENCE: 6

```
gggggcggtg gtagcggtgg cgggggctca ggcggaggtg ggagc                     45
```

<210> SEQ ID NO 7
<211> LENGTH: 534
<212> TYPE: PRT
<213> ORGANISM: Artificial Sequence
<220> FEATURE:
<223> OTHER INFORMATION: Fusion protein p75NTR-ECD-IL-33

<400> SEQUENCE: 7

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80
```

-continued

```
Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Gly Gly Gly Gly Ser Gly
                245                 250                 255

Gly Gly Gly Ser Gly Gly Gly Gly Ser Lys Pro Lys Met Lys Tyr Ser
            260                 265                 270

Thr Asn Lys Ile Ser Thr Ala Lys Trp Lys Asn Thr Ala Ser Lys Ala
        275                 280                 285

Leu Cys Phe Lys Leu Gly Lys Ser Gln Gln Lys Ala Lys Glu Val Cys
    290                 295                 300

Pro Met Tyr Phe Met Lys Leu Arg Ser Gly Leu Met Ile Lys Lys Glu
305                 310                 315                 320

Ala Cys Tyr Phe Arg Arg Glu Thr Thr Lys Arg Pro Ser Leu Lys Thr
                325                 330                 335

Gly Arg Lys His Lys Arg His Leu Val Leu Ala Ala Cys Gln Gln Gln
            340                 345                 350

Ser Thr Val Glu Cys Phe Ala Phe Gly Ile Ser Gly Val Gln Lys Tyr
        355                 360                 365

Thr Arg Ala Leu His Asp Ser Ser Ile Thr Gly Ile Ser Pro Ile Thr
    370                 375                 380

Glu Tyr Leu Ala Ser Leu Ser Thr Tyr Asn Asp Gln Ser Ile Thr Phe
385                 390                 395                 400

Ala Leu Glu Asp Glu Ser Tyr Glu Ile Tyr Val Glu Asp Leu Lys Lys
                405                 410                 415

Asp Glu Lys Lys Asp Lys Val Leu Leu Ser Tyr Tyr Glu Ser Gln His
            420                 425                 430

Pro Ser Asn Glu Ser Gly Asp Gly Val Asp Gly Lys Met Leu Met Val
        435                 440                 445

Thr Leu Ser Pro Thr Lys Asp Phe Trp Leu His Ala Asn Asn Lys Glu
    450                 455                 460

His Ser Val Glu Leu His Lys Cys Glu Lys Pro Leu Pro Asp Gln Ala
465                 470                 475                 480

Phe Phe Val Leu His Asn Met His Ser Asn Cys Val Ser Phe Glu Cys
                485                 490                 495
```

-continued

```
Lys Thr Asp Pro Gly Val Phe Ile Gly Val Lys Asp Asn His Leu Ala
            500                 505                 510

Leu Ile Lys Val Asp Ser Ser Glu Asn Leu Cys Thr Glu Asn Ile Leu
        515                 520                 525

Phe Lys Leu Ser Glu Thr
    530
```

<210> SEQ ID NO 8
<211> LENGTH: 1605
<212> TYPE: DNA
<213> ORGANISM: Artificial Sequence
<220> FEATURE:
<223> OTHER INFORMATION: p75NTR-ECD-IL-33

<400> SEQUENCE: 8

```
atgggtgcag gggcgaccgg tagggcgatg gatgggcccc ggctgttact gcttttgcta      60

ttaggcgttt ctcttggcgg ggcgaaggag gcgtgcccga cagggctcta cacgcacagc     120

ggggagtgct gtaaggcatg taacttgggc gaaggcgtgg cacaaccctg tggcgccaac     180

cagactgtat gcgagccctg tctagattct gtgactttct cggatgtagt ctcggctaca     240

gaaccctgca agccttgtac cgaatgcgta gggcttcagt cgatgtcggc tccgtgtgtc     300

gaggctgacg acgcggtgtg tcgctgtgcc tacggctact accaagacga aacaacggga     360

cgctgcgagg cttgtcgcgt atgtgaagct gggagcggcc ttgtgttttc ttgtcaagat     420

aagcaaaaca cagtttgtga agaatgcccc gacgggactt acagcgacga ggcaaatcat     480

gtggaccctt gtcttccgtg taccgtttgc gaggacactg agcgacaact aagggaatgc     540

accaggtggg cagacgccga atgcgaagaa ataccgggca gatggataac acgctccacg     600

ccgcctgagg gtagcgattc cacagctcca tccacacagg agcctgaagc tccaccggaa     660

caggatttaa tcgcttctac cgtggccgga gtggtcacaa cagtcatggg gtcgtcacaa     720

cctgtagtaa cacgagggac gacagacaac gggggcggtg gtagcggtgg cgggggctca     780

ggcggaggtg ggagcaaacc taaaatgaaa tattcgacta acaaaattag taccgcgaaa     840

tggaaaaaca ccgcgtcaaa ggcgctttgc tttaagcttg gcaagtcgca gcagaaagcg     900

aaagaagtct gtccaatgta tttcatgaaa ctgcggtcgg ggttaatgat taagaaagag     960

gcatgttatt ttagacgcga gaccactaag cgcccctctc tcaagacagg tcgtaaacac    1020

aaacgtcacc tggtgctagc cgcttgtcag cagcaatcta ctgtcgagtg ttttgctttc    1080

gggatcagcg gggtgcaaaa gtacacaagg gcgctgcatg acagtagcat tactggtata    1140

agtccaataa cagagtatct tgcttcactc agtacttata acgatcagtc cataacgttc    1200

gcactggagg acgaatcata cgagatctac gtagaagatc tcaagaaaga cgaaaaaaaa    1260

gataaagtct tactgtcgta ttatgaatct cagcacccct cgaacgagag cggcgatgga    1320

gttgacggga agatgctaat ggttacttta tcccctacca aggatttttg gcttcatgcc    1380

aataataaag agcactccgt tgagctccat aaatgcgaaa aacccctccc ggatcaggcg    1440

ttttttgttc tccacaatat gcatagtaat tgcgtctcat tcgagtgtaa aacggaccca    1500

ggtgttttta tcggtgtgaa ggataaccac ctggctctga ttaaggtaga ctcaagtgaa    1560

aacttgtgca cggaaaacat actttttaag ttatcggaga cataa                    1605
```

<210> SEQ ID NO 9
<211> LENGTH: 18
<212> TYPE: DNA
<213> ORGANISM: Artificial Sequence
<220> FEATURE:

-continued

<223> OTHER INFORMATION: Forward primer F1

<400> SEQUENCE: 9
atgggtgcag gggcgacc 18

<210> SEQ ID NO 10
<211> LENGTH: 29
<212> TYPE: DNA
<213> ORGANISM: Artificial Sequence
<220> FEATURE:
<223> OTHER INFORMATION: Reverse primer R1

<400> SEQUENCE: 10
gttgtctgtc gtccctcgtg ttactacag 29

<210> SEQ ID NO 11
<211> LENGTH: 42
<212> TYPE: DNA
<213> ORGANISM: Artificial Sequence
<220> FEATURE:
<223> OTHER INFORMATION: Forward primer F2

<400> SEQUENCE: 11
aaacctaaaa tgaaatattc gactaacaaa attagtaccg cg 42

<210> SEQ ID NO 12
<211> LENGTH: 35
<212> TYPE: DNA
<213> ORGANISM: Artificial Sequence
<220> FEATURE:
<223> OTHER INFORMATION: Reverse primer R2

<400> SEQUENCE: 12
ttatgtctcg gatagcttga agagaatgtt ttcgg 35

<210> SEQ ID NO 13
<211> LENGTH: 27
<212> TYPE: DNA
<213> ORGANISM: Artificial Sequence
<220> FEATURE:
<223> OTHER INFORMATION: Forward primer F3

<400> SEQUENCE: 13
cgcggtacca tgggtgcagg ggcgacc 27

<210> SEQ ID NO 14
<211> LENGTH: 65
<212> TYPE: DNA
<213> ORGANISM: Artificial Sequence
<220> FEATURE:
<223> OTHER INFORMATION: Reverse primer R3

<400> SEQUENCE: 14
gctcccacct ccgcctgagc ccccgccacc gctaccaccg cccccgttgt ctgtcgtccc 60
tcgtg 65

<210> SEQ ID NO 15
<211> LENGTH: 62
<212> TYPE: DNA
<213> ORGANISM: Artificial Sequence
<220> FEATURE:
<223> OTHER INFORMATION: Reverse primer R4

<400> SEQUENCE: 15
cgcggtacta attttgttag tcgaatattt cattttaggt ttgctcaggc ggaggtggga 60
gc 62

<210> SEQ ID NO 16
<211> LENGTH: 62
<212> TYPE: DNA
<213> ORGANISM: Artificial Sequence
<220> FEATURE:
<223> OTHER INFORMATION: Forward primer F5

<400> SEQUENCE: 16
gctcccacct ccgcctgagc aaacctaaaa tgaaatattc gactaacaaa attagtaccg 60
cg 62

<210> SEQ ID NO 17
<211> LENGTH: 44
<212> TYPE: DNA
<213> ORGANISM: Artificial Sequence
<220> FEATURE:
<223> OTHER INFORMATION: Reverse primer R5

<400> SEQUENCE: 17
acgtctagat tatgtctcgg atagcttgaa gagaatgttt tcgg 44

<210> SEQ ID NO 18
<211> LENGTH: 8
<212> TYPE: PRT
<213> ORGANISM: Artificial Sequence
<220> FEATURE:
<223> OTHER INFORMATION: Flag tag

<400> SEQUENCE: 18

Asp Tyr Lys Asp Asp Asp Asp Lys
1               5

<210> SEQ ID NO 19
<211> LENGTH: 24
<212> TYPE: DNA
<213> ORGANISM: Artificial Sequence
<220> FEATURE:
<223> OTHER INFORMATION: Flag tag

<400> SEQUENCE: 19
gattacaaag atgacgatga taaa 24

<210> SEQ ID NO 20
<211> LENGTH: 22
<212> TYPE: PRT
<213> ORGANISM: Artificial Sequence
<220> FEATURE:
<223> OTHER INFORMATION: Flag tag

<400> SEQUENCE: 20

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 21
<211> LENGTH: 66
<212> TYPE: DNA
<213> ORGANISM: Artificial Sequence
<220> FEATURE:
<223> OTHER INFORMATION: Flag tag

<400> SEQUENCE: 21
gactacaaag accatgacgg tgattataaa gatcatgaca tcgactacaa ggatgacgat 60
gacaag 66

<210> SEQ ID NO 22
<211> LENGTH: 45
<212> TYPE: DNA
<213> ORGANISM: Artificial Sequence
<220> FEATURE:
<223> OTHER INFORMATION: F6

<400> SEQUENCE: 22
atggattaca aagatgacga tgataaaggt gcaggggcga ccggt 45

<210> SEQ ID NO 23
<211> LENGTH: 44
<212> TYPE: DNA
<213> ORGANISM: Artificial Sequence
<220> FEATURE:
<223> OTHER INFORMATION: F7

<400> SEQUENCE: 23
cgcggtacca tggattacaa agatgacgat gataaaggtg cagg 44

<210> SEQ ID NO 24
<211> LENGTH: 54
<212> TYPE: DNA
<213> ORGANISM: Artificial Sequence
<220> FEATURE:
<223> OTHER INFORMATION: Forward primer F8

<400> SEQUENCE: 24
cgcggtacca tggattacaa agatgacgat gataaaggtg caggggcgac cggt 54

<210> SEQ ID NO 25
<211> LENGTH: 41
<212> TYPE: DNA
<213> ORGANISM: Artificial Sequence
<220> FEATURE:
<223> OTHER INFORMATION: Reverse primer R8

<400> SEQUENCE: 25
acgtctagat tagttgtctg tcgtccctcg tgttactaca g 41

<210> SEQ ID NO 26
<211> LENGTH: 78
<212> TYPE: DNA
<213> ORGANISM: Artificial Sequence
<220> FEATURE:
<223> OTHER INFORMATION: Forward primer F9

<400> SEQUENCE: 26
cgcggtacca tggattacaa agatgacgat gataaaaaac ctaaaatgaa atattcgact 60
aacaaaatta gtaccgcg 78

<210> SEQ ID NO 27
<211> LENGTH: 44
<212> TYPE: DNA
<213> ORGANISM: Artificial Sequence
<220> FEATURE:
<223> OTHER INFORMATION: Reverse primer R9

<400> SEQUENCE: 27
acgtctagat tatgtctcgg atagcttgaa gagaatgttt tcgg 44

FUSION PROTEIN FOR TREATING ALZHEIMER'S DISEASE

CROSS-REFERENCE TO RELATED APPLICATIONS

This application is a § 371 of International Application No. PCT/CN2017/092850, filed Jul. 13, 2017, which claims priority to Chinese Patent Application No. 201610365327., filed May 26, 2016.

INCORPORATION-BY-REFERENCE OF MATERIAL SUBMITTED IN ELECTRONIC FORM

Incorporated herein by reference in its entirety is the Sequence Listing submitted via EFS-Web as a text file named EX181002PPC-US_SEQUENCE_LISTING_20181212_ST25, created Dec. 12, 2018, and having a size of 20,480 bytes.

TECHNICAL FIELD

The present invention relates to the field of biomedical technology, and in particular to a fusion protein for preventing and treating Alzheimer's disease, a preparation method and an application thereof.

BACKGROUND

Alzheimer's disease (AD) is typically referred to as "senile dementia". The prevalence of AD has increased with the intensification of aging and the rapid increase in the corresponding elderly population since Alzheimer's disease was discovered in the $20^{th}$ century. The prevention and treatment of AD has become the focus of attention of various governments and medical communities.

AD is a neurodegenerative disease with insidious onset and progressive development. However its exact pathogenesis is still unknown. There are many hypotheses about the etiology of AD, among which the beta-amyloid cascade hypothesis is dominant. The aggradation of amyloid beta-peptide (Aβ) plaque found in the brains is the key histopathological characteristic of AD. Aβ is the main component of amyloid plaques, which is composed of 39-43 amino acid residues, among which Aβ40 and Aβ42 are dominant Aβ is derived from its precursor protein (Amyloid precursor protein, APP) and is generated by hydrolysis of APP by β- and γ-secretase respectively. Under the pathological conditions, Aβ aggregates and precipitates to form amyloid plaques due to the excessive production of Aβ resulting from abnormal APP metabolism, or disorders in Aβ clearance. The neurotrophin receptor p75 (p75NTR) binds to Aβ and its polymers to mediate the neurotoxic reaction of β-amyloid peptide, inducing the body to produce an inflammatory response, leading to pathology and apoptosis in neurons and promoting the onset of AD and further deterioration of the condition. The soluble Aβs or their oligomers, insoluble Aβ fibrils and plaques have neurotoxic effects. Any method that can prevent the excessive production and aggregation of Aβ in the brain and block the binding of p75NTR to Aβ that mediates a neurotoxic reaction can achieve the goal of preventing the AD onset and alleviating the AD condition or preventing the deterioration of AD condition.

p75NTR, p75 neurotrophin receptor, is a transmembrane glycoprotein with a molecular mass of 75 kDa and consists of 427 amino acids, comprising a signal peptide with 28 amino acids, a cysteine-rich extracellular domain, a hydrophobic transmembrane domain and a basic amino acid-rich intracellular domain with 155 amino acids. Its extracellular domain (p75NTR extracellular domain, p75NTR-ECD) consists of four cysteine-rich repeat domains (CRDs), each of which contains a repeat structure consisting of 40 amino acids and six cysteines. The extracellular domain is modified by N- and O-glycosylation after translation. The second repeat sequence is required for binding to neurotrophins (NTs) and Aβ. Its transmembrane domain consists of a single chain comprising 22 amino acids and is involved in the phosphorylation of p75NTR. p75NTR is cleaved by TACE enzyme (TNF-alpha converting enzyme) to release its extracellular domain p75NTR-ECD.

According to the principle that free p75NTR-ECD can bind to Aβ to prevent p75NTR from binding to Aβ to produce neurotoxicity, Yanjiang Wang and Xinfu Zhou designed a p75NTR-ECD and a p75NTR-ECD-FC for the prevention and treatment of AD in the Chinese patent ZL201010561284.3; and Yongtang Wang et al. designed a p75NTR-ECD-FC for promoting the regeneration and functional recovery of injured central nerves in the Chinese under application patent 201210053808.7. The p75NTR-ECD and p75NTR-ECD-FC designed and prepared by Yanjiang Wang and Xinfu Zhou, and Yongtang Wang et al. have the following defects; (1) Prokaryotic expression systems are used to prepare target proteins and none of the products were subjected to post-translational modification of glycosylation, so that the original physical and chemical properties of p75NTR-ECD and the native spatial conformation of protein can not be maintained. Therefore, there will be no guarantee that the prepared proteins have effective biological activity for clinical treatment of AD. (2) The p75NTR-ECD-FC is a fusion protein of p75NTR-ECD and the FC fragment of human immunoglobulin, in which the FC fragment can induce antibody-dependent cell-mediated cytotoxicity (ADCC) in vivo and the own immune system attack to the neurons, and finally promote the onset of AD, the progression and deterioration of AD. Therefore it fails to achieve the purpose of preventing and treating AD. (3) The FC fragment of p75NTR-ECD-FC bears immunogenicity and can induce the production of anti-FC antibodies, which promote and result in the ineffectiveness or rapid degradation of ECD. (4) The p75NTR-ECD and p75NTR-ECD-FC only contain ECD, thus they are only able to bind to Aβ but not able to induce the body to promote Aβ degradation. Therefore they are inefficient in preventing and treating AD.

Interleukin-33 (IL-33) is a cytokine belonging to the interleukin-1 (IL-1) family discovered in 2005. It shares a similar gene sequence with IL-1β and IL-18 that are the members of the IL-1 family. IL-33 is an important regulator of the innate immune response and the infiltration and activation of immune cells. With a molecular weight of approximately 18 kDa, IL-33 contains 270 amino acids and comprises an N-terminal nuclear localization signal, a helix-turn-helix motif and a C-terminus. IL-33 binds to a heterodimeric receptor complex consisting of ST2 and IL-1RAcP to trigger a cascade reaction of intracellular signaling pathways comprising myeloid differentiation factor 88 (MyD88) and NF-κB, and selectively activate Type 2 helper T cells, mast cells, neutrophils and macrophages. In the central nervous system (CNS), IL-33 is expressed by the oligodendrocytes, while ST2 is mainly expressed by the microglias and the astrocytes. IL-33 is a pluripotent and pleiotropic cytokine that plays an essential regulatory role in infection, inflammation and autoimmune diseases. In 2009, Chapuis J, et al. found through genetic studies that the IL-33 expression in the brains of AD patients was significantly reduced, and that the three single nucleotide polymorphisms (SNPs) of IL-33 gene were closely related to a decrease in the risk of the occurrence and progression of AD (Chapuis J, et al., 2009. Transcriptomic and genetic studies identify IL-33 as a candidate gene for Alzheimer's disease. Mol Psychiatry 14(11):1004-1016). In 2008, Miller, A M, et al. found that IL-33 had a protective function in preventing atherosclerosis which was an important risk factor for the onset and progression of AD (Miller, A. M., Xu, D., Asquith, D. L., Denby, L., Li, Y, Sattar, N., Baker, A. H., McInnes, I. B., Liew, F. Y., 2008. IL-33 reduces the development of atherosclerosis. J. Exp. Med. 205, 339246). This protective effect may be associated with the down-regulation of Aβ secretion by IL-33. In 2011, Yasuoka, S., et al. found that IL-33 induced the proliferation of microglia and the production of cytokines IL-1β, TNFα and IL-10 in a dose-dependent manner (Yasuoka, S., Kawanokuchi, J., Parajuli, B., Jin, S., Doi, Y, Noda, M., Sonobe, Y, Takeuchi, H., Mizuno, T., Suzumura, A., 2011. Production and functions of IL-33 in the central nervous system. Brain Res. 1385, 8-17). Taken together, these studies have found that IL-33 can prevent the onset, progression and deterioration of AD and thus has potential therapeutic effects on the prevention and treatment of AD.

Based on the fact that there are still no effective drugs and treatments for AD and exist the deficiencies in the development of p75NTR-ECD and p75NTR-ECD-FC for preventing and treating AD, it is crucial to find an efficacious drug for the prevention and treatment of AD.

SUMMARY OF THE PRESENT INVENTION

In order to overcome the deficiencies in the prior art, the present invention provides a fusion protein for preventing and treating Alzheimer's disease, and a preparation method and application thereof.

The present invention will solve the technical problems through the following technical solutions:

A fusion protein p5NTR-ECD-IL-33 for preventing and treating Alzheimer's disease, comprising p75NTR-ECD (the extracellular domain of human p75NTR), human IL-33 and a linker peptide which is linked to the carboxyl terminus of the p75NTR-ECD and the amino terminus of the human IL-33, respectively; the p75NTR-ECD has the amino acid sequence as shown in SEQ ID NO. 1, and the nucleotide sequence as shown in SEQ ID NO. 2; the human IL-33 has the amino acid sequence as shown in SEQ ID NO. 3, and the nucleotide sequence as shown in SEQ ID NO. 4;

A method for constructing the fusion protein, comprising the step of linking the carboxyl terminus of p75NTR-ECD which is the extracellular domain of human p75NTR and the amino terminus of human IL-33 via a linker peptide. The p75NTR-ECD which is the extracellular domain of human p75NTR has an amino acid sequence as shown in SEQ ID NO. 1, and a nucleotide sequence as shown in SEQ ID NO. 2; the human IL-33 has an amino acid sequence as shown in SEQ ID NO. 3, and a nucleotide sequence as shown in SEQ ID NO. 4.

A expression vector for the fusion protein, comprising a mRNA, a DNA plasmid vector and a viral vector.

A method for preparing a DNA plasmid vector for the fusion protein, comprising the following steps:

(1) cloning to obtain a gene fragment of p75NTR-ECD which is the extracellular domain of human p75NTR;

(2) cloning to obtain a gene fragment of human IL-33;

(3) obtaining a gene fragment encoding p75NTR-ECD-Linker by a PCR reaction, wherein the carboxyl terminus of p75NTR-ECD is linked to the amino terminus of the Linker, and the gene fragment of the Linker is derived from the reverse primer sequence of the PCR reaction;

(4) linking the carboxyl terminus of p75NTR-ECD-Linker to the amino terminus of human IL-33 by an overlapping PCR reaction to obtain a gene fragment of fusion protein p75NTR-ECD-IL-33, wherein the p75NTR-ECD-Linker gene fragment contains a restriction site at the 5'-end and the IL-33 gene fragment contains another restriction site at the 3'-end;

(5) enzymatically digesting the gene fragment of fusion protein p75NTR-ECD-IL-33, inserting the gene fragment into a plasmid vector between two corresponding restriction sites, transforming the vector to a host strain, extracting positive plasmids and sequencing the inserted target gene to obtain a DNA plasmid vector comprising the target gene of p75NTR-ECD-IL-33;

Alternatively, steps (3) and (4) can be replaced by (3') and (4'), respectively:

(3') obtaining a gene fragment encoding IL-33-Linker by a PCR reaction, wherein the amino terminus of IL-33 is linked to the carboxyl terminus of the Linker, of which the gene fragment comes from the reverse primer sequence in the PCR reaction;

(4') linking the amino terminus of IL-33-Linker to the carboxyl terminus of human p75NTR-ECD by an overlapping PCR reaction to obtain a gene fragment of fusion protein p75NTR-ECD-IL-33, wherein the IL-33-Linker gene fragment comprises a restriction site at the 5'-end and the p75NTR-ECD gene fragment comprises another restriction site at the 3'-end.

A method for preparing a target protein which comprises a p75NTR-ECD (extracellular domain of human p75NTR), a human IL-33 and a fusion protein p5NTR-ECD-IL-33 comprising the following steps:

(1) using the gene fragment of target protein as a template; employing the plasmid vector as a vector; using two restriction sites of the plasmid vector as insertion sites of the target gene; linking a Flag tag to the amino terminus of the target protein; using a PCR reaction to obtain a expression plasmid for the target protein with Flag tag if the target protein is human p75NTR-ECD or human IL-33: plasmid VFlag-p75NTR-ECD or plasmid VFlag-IL-33; employing an overlapping PCR reaction to obtain the expression plasmid for p75NTR-ECD-IL-33 with Flag tag if the target protein is fusion protein p5NTR-ECD-IL-33: plasmid V Flag-p75NTR-ECD-IL-33.

(2) transfecting the expression plasmid into eukaryotic cells to obtain a stable cell line expressing the target protein;

(3) extracting and preliminary purifying the target protein from the cells which stably express the target protein to obtain a crude solution of the target protein;

(4) removing the Flag tag from the target protein with Flag tag in the crude solution to obtain a purified target protein.

The application of the DNA plasmid vector of the fusion protein or the fusion protein in the preparation of medicaments for preventing and treating Alzheimer's disease.

A medicament for preventing and treating Alzheimer's disease, which is the fusion protein, or a mRNA liposome expressing the fusion protein, or a viral vector carrying the gene encoding the fusion protein.

Compared with the prior art, the present invention has the following beneficial effects. The present invention designs and constructs a fusion protein (p75NTR-ECD-IL-33) for preventing and treating Alzheimer's disease which is formed by linking p75NTR-ECD (extracellular domain of p75NTR) to IL-33 via a linker peptide (Linker). The invention not only overcomes the deficiencies in the instability, immunogenicity and antibody-dependent cell-mediated cytotoxicity (ADCC) of the p75NTR-ECD or its fusion protein p75NTR-ECD-FC, but also makes up for the disadvantages of the single mechanism that functions only through the combination with Aβ for the prevention and treatment of AD. Meanwhile, the functions of both IL-33 and p75NTR-ECD are combined and the biological activity for the prevention and treatment of AD is significantly enhanced by improving the stability and the synergistic effects of both.

Specifically, the invention has the following advantages: (1) The p75NTR-ECD-IL-33 has the biological functions of both p75NTR-ECD and IL-33. The p75NTR-ECD in the p75NTR-ECD-IL-33 binds to Aβ and its aggregates to prevent p75NTR from binding to Aβ and its aggregates and therefore protect central neurons from the neurotoxicity of Aβ. The IL-33 in the p75NTR-ECD-IL-33 induces the body to reduce the secretion of Aβ and promote the degradation of Aβ, and thus prevents the onset, the progression and the deterioration of AD. (2) The p75NTR-ECD-IL-33 is a fusion protein that can effectively enhance the stabilities of p75NTR-ECD and IL-33 and prolong their half-lives both in vitro and in vivo. (3) P75NTR-ECD-IL-33 can synergize the functions of p75NTR-ECD and IL-33 in the prevention and treatment of AD.

The p75NTR-ECD-IL-33 enables IL-33 to target Aβ precisely via the binding of p75NTR-ECD to Aβ, and induce the direct endocytosis of Aβ and its oligomers, or the secretion of enzymes to degrade Aβ, thereby improving the efficiency of the Aβ degradation. As a result, the biological activity of the fusion protein p75NTR-ECD-IL-33 is significantly increased compared with that of its monomers p75NTR-ECD and IL-33. (4) The P75NTR-ECD-IL-33 can be constructed to be expressed in eukaryotic cells and human body, so that p75NTR-ECD and IL-33 in p75NTR-ECD-IL-33 can be adequately glycosylated after translation, thus maintaining their native physical and chemical properties and biological functions under physiological conditions. (5) The p75NTR-ECD-IL-33 overcomes the shortcomings of the immunogenicity and the antibody-dependent cell-mediated cytotoxicity (ADCC) of the FC in p75NTR-ECD-FC so that the p75NTR-ECD-IL-33 is expected to become a safe and effective drug for the prevention and treatment of AD and fill the gap that there are still no effective drugs for preventing and treating AD.

DETAILED DESCRIPTION

Figure 1:
FIG. 1 is a schematic diagram showing the construction of the fusion protein p75NTR-ECD-IL-33 in a specific embodiment of the present invention.
Figure 2:
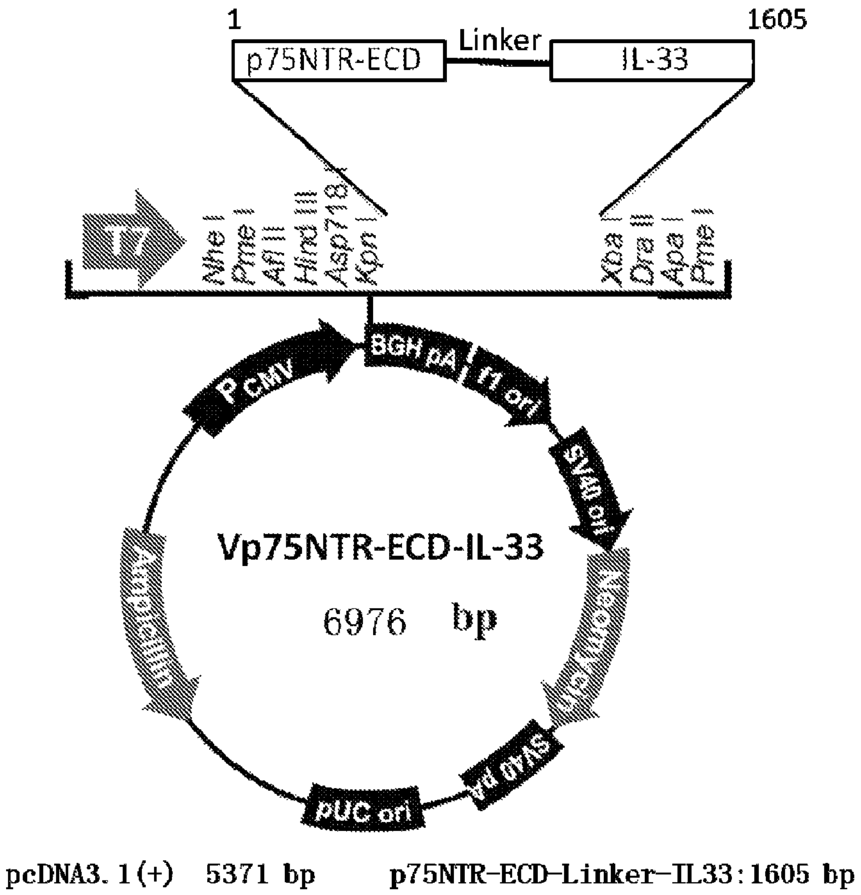
FIG. 2 is a schematic diagram showing the plasmid vector of the fusion protein p75NTR-ECD-IL-33 in a specific embodiment of the present invention.

The present invention will be further described with reference to the accompanying drawings and according to the preferred embodiments.

The present invention designs and constructs a fusion protein (also known as Chimeric antigen receptor protein (CAR-P), which is named as p75NTR-ECD-IL-33) for the prevention and treatment of Alzheimer's disease. The "linker peptide" and "linker" herein have the same concept. The "human p75 neurotrophin receptor" may be abbreviated as "p75NTR"; and the "human interleukin-33" may be abbreviated as "human IL-33" or "IL-33".

For preventing and treating Alzheimer's disease, the present invention provides a fusion protein comprising a p75NTR-ECD which is the extracellular domain of human p75NTR, a human IL-33 and a linker peptide which is linked to the carboxyl terminus of the p75NTR-ECD and the amino terminus of the human IL-33, respectively; the p75NTR-ECD has an amino acid sequence as shown in SEQ ID NO. 1, and a nucleotide sequence as shown in SEQ ID NO. 2; the human IL-33 has an amino acid sequence as shown in SEQ ID NO. 3, and a nucleotide sequence as shown in SEQ ID NO. 4. Specifically:

The p75NTR-ECD has an amino acid sequence (250 aa):

```
Met Gly Ala Gly Ala Thr Gly Arg Ala Met Asp Gly
Pro Arg Leu Leu Leu Leu Leu Leu Leu Gly Val Ser
Leu Gly Gly Ala Lys Glu Ala Cys Pro Thr Gly Leu
Tyr Thr His Ser Gly Glu Cys Cys Lys Ala Cys Asn
Leu Gly Glu Gly Val Ala Gln Pro Cys Gly Ala Asn
Gln Thr Val Cys Glu Pro Cys Leu Asp Ser Val Thr
Phe Ser Asp Val Val Ser Ala Thr Glu Pro Cys Lys
Pro Cys Thr Glu Cys Val Gly Leu Gln Ser Met Ser
Ala Pro Cys Val Glu Ala Asp Asp Ala Val Cys Arg
Cys Ala Tyr Gly Tyr Tyr Gln Asp Glu Thr Thr Gly
Arg Cys Glu Ala Cys Arg Val Cys Glu Ala Gly Ser
Gly Leu Val Phe Ser Cys Gln Asp Lys Gln Asn Thr
Val Cys Glu Glu Cys Pro Asp Gly Thr Tyr Ser Asp
Glu Ala Asn His Val Asp Pro Cys Leu Pro Cys Thr
Val Cys Glu Asp Thr Glu Arg Gln Leu Arg Glu Cys
Thr Arg Trp Ala Asp Ala Glu Cys Glu Glu Ile Pro
```

-continued

Gly Arg Trp Ile Thr Arg Ser Thr Pro Pro Glu Gly
Ser Asp Ser Thr Ala Pro Ser Thr Gln Glu Pro Glu
Ala Pro Pro Glu Gln Asp Leu Ile Ala Ser Thr Val
Ala Gly Val Val Thr Thr Val Met Gly Ser Ser Gln
Pro Val Val Thr Arg Gly Thr Thr Asp Asn.

The p75NTR-ECD has a nucleotide sequence (750 bp):

ATGGGTGCAGGGGCGACCGGTAGGGCGATGGATGGGCCCCGGCTGTTA
CTGCTTTTGCTATTAGGCGTTTCTCTTGGCGGGGCGAAGGAGGCGTGC
CCGACAGGGCTCTACACGCACAGCGGGGAGTGCTGTAAGGCATGTAAC
TTGGGCGAAGGCGTGGCACAACCCTGTGGCGCCAACCAGACTGTATGC
GAGCCCTGTCTAGATTCTGTGACTTTCTCGGATGTAGTCTCGGCTACA
GAACCCTGCAAGCCTTGTACCGAATGCGTAGGGCTTCAGTCGATGTCG
GCTCCGTGTGTCGAGGCTGACGACGCGGTGTGTCGCTGTGCCTACGGC
TACTACCAAGACGAAACAACGGGACGCTGCGAGGCTTGTCGCGTATGT
GAAGCTGGGAGCGGCCTTGTGTTTTCTTGTCAAGATAAGCAAAACACA
GTTTGTGAAGAATGCCCCGACGGGACTTACAGCGACGAGGCAAATCAT
GTGGACCCTTGTCTTCCGTGTACCGTTTGCGAGGACACTGAGCGACAA
CTAAGGGAATGCACCAGGTGGGCAGACGCCGAATGCGAAGAAATACCG
GGCAGATGGATAACACGCTCCACGCCGCCTGAGGGTAGCGATTCCACA
GCTCCATCCACACAGGAGCCTGAAGCTCCACCGGAACAGGATTTAATC
GCTTCTACCGTGGCCGGAGTGGTCACAACAGTCATGGGGTCGTCACAA
CCTGTAGTAACACGAGGGACGACAGACAAC.

The human IL-33 has an amino acid sequence (269 aa):

Lys Pro Lys Met Lys Tyr Ser Thr Asn Lys Ile Ser
Thr Ala Lys Trp Lys Asn Thr Ala Ser Lys Ala Leu
Cys Phe Lys Leu Gly Lys Ser Gln Gln Lys Ala Lys
Glu Val Cys Pro Met Tyr Phe Met Lys Leu Arg Ser
Gly Leu Met Ile Lys Lys Glu Ala Cys Tyr Phe Arg
Arg Glu Thr Thr Lys Arg Pro Ser Leu Lys Thr Gly
Arg Lys His Lys Arg His Leu Val Leu Ala Ala Cys
Gln Gln Gln Ser Thr Val Glu Cys Phe Ala Phe Gly
Ile Ser Gly Val Gln Lys Tyr Thr Arg Ala Leu His
Asp Ser Ser Ile Thr Gly Ile Ser Pro Ile Thr Glu
Tyr Leu Ala Ser Leu Ser Thr Tyr Asn Asp Gln Ser
Ile Thr Phe Ala Leu Glu Asp Glu Ser Tyr Glu Ile
Tyr Val Glu Asp Leu Lys Lys Asp Glu Lys Lys Asp
Lys Val Leu Leu Ser Tyr Tyr Glu Ser Gln His Pro
Ser Asn Glu Ser Gly Asp Gly Val Asp Gly Lys Met
Leu Met Val Thr Leu Ser Pro Thr Lys Asp Phe Trp

-continued

Leu His Ala Asn Asn Lys Glu His Ser Val Glu Leu
His Lys Cys Glu Lys Pro Leu Pro Asp Gln Ala Phe
Phe Val Leu His Asn Met His Ser Asn Cys Val Ser
Phe Glu Cys Lys Thr Asp Pro Gly Val Phe Ile Gly
Val Lys Asp Asn His Leu Ala Leu Ile Lys Val Asp
Ser Ser Glu Asn Leu Cys Thr Glu Asn Ile Leu Phe
Lys Leu Ser Glu Thr.

The human IL-33 has a nucleotide sequence (containing a stop codon TAA, 810 bp):

AAACCTAAAATGAAATATTCGACTAACAAAATTAGTACCGCGAAATGG
AAAAACACCGCGTCAAAGGCGCTTTGCTTTAAGCTTGGCAAGTCGCAG
CAGAAAGCGAAAGAAGTCTGTCCAATGTATTTCATGAAACTGCGGTCG
GGGTTAATGATTAAGAAAGAGGCATGTTATTTTAGACGCGAGACCACT
AAGCGCCCCTCTCTCAAGACAGGTCGTAAACACAAACGTCACCTGGTG
CTAGCCGCTTGTCAGCAGCAATCTACTGTCGAGTGTTTTGCTTTCGGG
ATCAGCGGGGTGCAAAAGTACACAAGGGCGCTGCATGACAGTAGCATT
ACTGGTATAAGTCCAATAACAGAGTATCTTGCTTCACTCAGTACTTAT
AACGATCAGTCCATAACGTTCGCACTGGAGGACGAATCATACGAGATC
TACGTAGAAGATCTCAAGAAAGACGAAAAAAAAGATAAAGTCTTACTG
TCGTATTATGAATCTCAGCACCCTTCGAACGAGAGCGGCGATGGAGTT
GACGGGAAGATGCTAATGGTTACTTTATCCCCTACCAAGGATTTTTGG
CTTCATGCCAATAATAAAGAGCACTCCGTTGAGCTCCATAAATGCGAA
AAACCCCTCCCGGATCAGGCGTTTTTTGTTCTCCACAATATGCATAGT
AATTGCGTCTCATTCGAGTGTAAAACGGACCCAGGTGTTTTTATCGGT
GTGAAGGATAACCACCTGGCTCTGATTAAGGTAGACTCAAGTGAAAAC
TTGTGCACGGAAAACATACTTTTTAAGTTATCGGAGACATAA.

The method for constructing a fusion protein p75NTR-ECD-IL-33 comprises a step of linking the carboxyl terminus of p75NTR-ECD which is the extracellular domain of human p75NTR and the amino terminus of human IL-33 via a linker peptide (Linker). A specific linking method is shown in FIG. 1.

In a preferred embodiment, the Linker is selected to be a flexible linker peptide or a rigid linker peptide. Wherein, the flexible linker peptide is preferably selected as: (Gly Gly Gly Gly Ser)n, wherein n is an integer between 1 and 6; or (Gly Gly Gly Gly Thr)n, wherein n is an integer between 1 and 6. The rigid linker peptide is selected as: (Glu Ala Ala Ala Lys)m, wherein m is an integer between 1 and 6; or a proline-rich sequence (XPro)q, wherein q is an integer between 3 and 10, and X is any amino acid which preferably comprises lysine, alanine and glutamic acid.

In a more preferred embodiment, the Linker has an amino acid sequence (15 aa) as shown in SEQ ID NO. 5: Gly Gly Gly Gly Ser Gly Gly Gly Gly Ser Gly Gly Gly Gly Ser, and a nucleotide sequence (45 bp) as shown in SEQ ID NO. 6:

GGGGGCGGTGGTAGCGGTGGCGGGGGCTCAGGCGGAGGTGGGAGC.

Among the preferred Linkers, the Gly is a non-polar small amino acid that can provide the flexibility for the fusion protein and make it easier for the fusion protein to fold into a natural conformation with a biological activity after translation without affecting the biological functions of p75NTR-ECD and ECD-IL-3 in p75NTR-ECD-IL-33; and the Ser is a polar small amino acid that can form hydrogen bonds with $H_2O$ molecules, increase the solubility and stability of the linker peptide in aqueous solutions, and prevent the Linker from interfering with the biological function of each protein in the fusion protein. Of course, in other embodiments, Ser can also be replaced with threonine (Thr).

Accordingly, the fusion protein p75NTR-ECD-IL-33 which is constructed by using the preferred Linker has an amino acid sequence (534 aa) as shown in SEQ ID NO. 7 and a nucleotide sequence (comprising a start codon and a stop codon, 1605 bp) as shown in SEQ ID NO. 8 respectively:

```
Met Gly Ala Gly Ala Thr Gly Arg Ala Met Asp Gly
Pro Arg Leu Leu Leu Leu Leu Leu Leu Gly Val Ser
Leu Gly Gly Ala Lys Glu Ala Cys Pro Thr Gly Leu
Tyr Thr His Ser Gly Glu Cys Cys Lys Ala Cys Asn
Leu Gly Glu Gly Val Ala Gln Pro Cys Gly Ala Asn
Gln Thr Val Cys Glu Pro Cys Leu Asp Ser Val Thr
Phe Ser Asp Val Val Ser Ala Thr Glu Pro Cys Lys
Pro Cys Thr Glu Cys Val Gly Leu Gln Ser Met Ser
Ala Pro Cys Val Glu Ala Asp Asp Ala Val Cys Arg
Cys Ala Tyr Gly Tyr Tyr Gln Asp Glu Thr Thr Gly
Arg Cys Glu Ala Cys Arg Val Cys Glu Ala Gly Ser
Gly Leu Val Phe Ser Cys Gln Asp Lys Gln Asn Thr
Val Cys Glu Glu Cys Pro Asp Gly Thr Tyr Ser Asp
Glu Ala Asn His Val Asp Pro Cys Leu Pro Cys Thr
Val Cys Glu Asp Thr Glu Arg Gln Leu Arg Glu Cys
Thr Arg Trp Ala Asp Ala Glu Cys Glu Glu Ile Pro
Gly Arg Trp Ile Thr Arg Ser Thr Pro Pro Glu Gly
Ser Asp Ser Thr Ala Pro Ser Thr Gln Glu Pro Glu
Ala Pro Pro Glu Gln Asp Leu Ile Ala Ser Thr Val
Ala Gly Val Val Thr Thr Val Met Gly Ser Ser Gln
Pro Val Val Thr Arg Gly Thr Thr Asp Asn Gly Gly
Gly Gly Ser Gly Gly Gly Gly Ser Gly Gly Gly Gly
Ser Lys Pro Lys Met Lys Tyr Ser Thr Asn Lys Ile
Ser Thr Ala Lys Trp Lys Asn Thr Ala Ser Lys Ala
Leu Cys Phe Lys Leu Gly Lys Ser Gln Gln Lys Ala
Lys Glu Val Cys Pro Met Tyr Phe Met Lys Leu Arg
Ser Gly Leu Met Ile Lys Lys Glu Ala Cys Tyr Phe
Arg Arg Glu Thr Thr Lys Arg Pro Ser Leu Lys Thr
Gly Arg Lys His Lys Arg His Leu Val Leu Ala Ala
```

-continued

```
Cys Gln Gln Gln Ser Thr Val Glu Cys Phe Ala Phe
Gly Ile Ser Gly Val Gln Lys Tyr Thr Arg Ala Leu
His Asp Ser Ser Ile Thr Gly Ile Ser Pro Ile Thr
Glu Tyr Leu Ala Ser Leu Ser Thr Tyr Asn Asp Gln
Ser Ile Thr Phe Ala Leu Glu Asp Glu Ser Tyr Glu
Ile Tyr Val Glu Asp Leu Lys Lys Asp Glu Lys Lys
Asp Lys Val Leu Leu Ser Tyr Tyr Glu Ser Gln His
Pro Ser Asn Glu Ser Gly Asp Gly Val Asp Gly Lys
Met Leu Met Val Thr Leu Ser Pro Thr Lys Asp Phe
Trp Leu His Ala Asn Asn Lys Glu His Ser Val Glu
Leu His Lys Cys Glu Lys Pro Leu Pro Asp Gln Ala
Phe Phe Val Leu His Asn Met His Ser Asn Cys Val
Ser Phe Glu Cys Lys Thr Asp Pro Gly Val Phe Ile
Gly Val Lys Asp Asn His Leu Ala Leu Ile Lys Val
Asp Ser Ser Glu Asn Leu Cys Thr Glu Asn Ile Leu
Phe Lys Leu Ser Glu Thr.
```

```
ATGGGTGCAGGGGCGACCGGTAGGGCGATGGATGGGCCCCGGCTGTTA
CTGCTTTTGCTATTAGGCGTTTCTCTTGGCGGGGCGAAGGAGGCGTGC
CCGACAGGGCTCTACACGCACAGCGGGGAGTGCTGTAAGGCATGTAAC
TTGGGCGAAGGCGTGGCACAACCCTGTGGCGCCAACCAGACTGTATGC
GAGCCCTGTCTAGATTCTGTGACTTTCTCGGATGTAGTCTCGGCTACA
GAACCCTGCAAGCCTTGTACCGAATGCGTAGGGCTTCAGTCGATGTCG
GCTCCGTGTGTCGAGGCTGACGACGCGGTGTGTCGCTGTGCCTACGGC
TACTACCAAGACGAAACAACGGGACGCTGCGAGGCTTGTCGCGTATGT
GAAGCTGGGAGCGGCCTTGTGTTTTCTTGTCAAGATAAGCAAAACACA
GTTTGTGAAGAATGCCCCGACGGGACTTACAGCGACGAGGCAAATCAT
GTGGACCCTTGTCTTCCGTGTACCGTTTGCGAGGACACTGAGCGACAA
CTAAGGGAATGCACCAGGTGGGCAGACGCCGAATGCGAAGAAATACCG
GGCAGATGGATAACACGCTCCACGCCGCCTGAGGGTAGCGATTCCACA
GCTCCATCCACACAGGAGCCTGAAGCTCCACCGGAACAGGATTTAATC
GCTTCTACCGTGGCCGGAGTGGTCACAACAGTCATGGGGTCGTCACAA
CCTGTAGTAACACGAGGGACGACAGACAACGGGGGCGGTGGTAGCGGT
GGCGGGGGCTCAGGCGGAGGTGGGAGCAAACCTAAAATGAAATATTCG
ACTAACAAAATTAGTACCGCGAAATGGAAAAACACCGCGTCAAAGGCG
CTTTGCTTTAAGCTTGGCAAGTCGCAGCAGAAAGCGAAAGAAGTCTGT
CCAATGTATTTCATGAAACTGCGGTCGGGGTTAATGATTAAGAAAGAG
GCATGTTATTTTAGACGCGAGACCACTAAGCGCCCCTCTCTCAAGACA
GGTCGTAAACACAAACGTCACCTGGTGCTAGCCGCTTGTCAGCAGCAA
TCTACTGTCGAGTGTTTTGCTTTCGGGATCAGCGGGGTGCAAAAGTAC
ACAAGGGCGCTGCATGACAGTAGCATTACTGGTATAAGTCCAATAACA
```

-continued

```
GAGTATCTTGCTTCACTCAGTACTTATAACGATCAGTCCATAACGTTC

GCACTGGAGGACGAATCATACGAGATCTACGTAGAAGATCTCAAGAAA

GACGAAAAAAAAGATAAAGTCTTACTGTCGTATTATGAATCTCAGCAC

CCTTCGAACGAGAGCGGCGATGGAGTTGACGGGAAGATGCTAATGGTT

ACTTTATCCCCTACCAAGGATTTTTGGCTTCATGCCAATAATAAAGAG

CACTCCGTTGAGCTCCATAAATGCGAAAAACCCCTCCCGGATCAGGCG

TTTTTTGTTCTCCACAATATGCATAGTAATTGCGTCTCATTCGAGTGT

AAAACGGACCCAGGTGTTTTTATCGGTGTGAAGGATAACCACCTGGCT

CTGATTAAGGTAGACTCAAGTGAAAACTTGTGCACGGAAAACATACTT

TTTAAGTTATCGGAGACATAA.
```

The invention also provides an expression vector for the fusion protein in the above embodiments which can be selected from one of the vectors comprising mRNA, DNA plasmid or virus vectors (comprising Lentivirus, adeno virus, adeno-associated virus, etc.).

The present invention also provides a method for preparing a DNA plasmid vector for the fusion protein, and in a specific embodiment the method comprises the following steps:

(1) cloning to obtain a gene fragment of p75NTR-ECD which is the extracellular domain of human p75NTR;

(2) cloning to obtain a gene fragment of human IL-33;

(3) obtaining a gene fragment encoding p75NTR-ECD-Linker by a PCR reaction, wherein the carboxyl terminus of p75NTR-ECD is linked to the amino terminus of the Linker, and the gene fragment of the Linker is derived from the reverse primer sequence of the PCR reaction;

(4) linking the carboxyl terminus of p75NTR-ECD-Linker to the amino terminus of human IL-33 by an overlapping PCR reaction to obtain a gene fragment of fusion protein p75NTR-ECD-IL-33, wherein the p75NTR-ECD-Linker gene fragment comprises a restriction site at the 5'-end and the IL-33 gene fragment comprises another restriction site at the 3'-end;

(5) enzymatically digesting the gene fragment of fusion protein p75NTR-ECD-IL-33, inserting the gene fragment into a plasmid vector between two corresponding restriction sites, transforming the vector to a host strain, extracting positive plasmids and sequencing the inserted target gene to obtain a DNA plasmid vector comprising the target gene of p75NTR-ECD-IL-33;

Alternatively, steps (3) and (4) can be replaced with (3') and (4'), respectively:

(3') obtaining a gene fragment encoding IL-33-Linker by a PCR reaction, wherein the amino terminus of IL-33 is linked to the carboxyl terminus of the Linker, of which the gene fragment comes from the reverse primer sequence in the PCR reaction;

(4') linking the amino terminus of IL-33-Linker to the carboxyl terminus of human p75NTR-ECD by an overlapping PCR reaction to obtain a gene fragment of fusion protein p75NTR-ECD-IL-33, wherein the IL-33-Linker gene fragment comprises a restriction site at the 5'-end and the p75NTR-ECD gene fragment comprises another restriction site at the 3'-end.

In a preferred embodiment, pcDNA3.1(+) can be selected as the plasmid vector in the step (5); and the gene fragment of fusion protein p75NTR-ECD-IL-33 is inserted into pcDNA3.1(+) between KpnI and XbaI restriction sites.

A preferred embodiment is described below to illustrate the processes of the construction and preparation of a DNA plasmid vector for the target gene of p75NTR-ECD-IL-33:

(1) The Gene fragment of p75ntr-ecd (containing the initial codon ATG, but not the stop codon TAA) was cloned from Human NGFR Gene cDNA, and the primers (5'-3') required for cloning are as follows:

```
Forward primer F1 as shown in SEQ ID NO. 9:
ATGGGTGCAGGGGCGACC;
and

reverse primer R1 as shown in SEQ ID NO. 10:
GTTGTCTGTCGTCCCTCGTGTTACTACAG.
```

(2) The gene fragment of human IL-33 (containing a stop codon TAA, but not a start codon ATG) was cloned from Human IL33 Gene cDNA. The primers (5'-3') required for cloning are shown as the following:

```
forward primer F2 as shown in SEQ ID NO. 11:
AAACCTAAAATGAAATATTCGACTAACAAAATTAGTACCGCG;
and

reverse primer R2 as shown in SEQ ID NO. 12:
TTATGTCTCGGATAGCTTGAAGAGAATGTTTTCGG.
```

(3) A gene fragment of p75NTR-ECD-Linker was obtained by a PCR reaction, wherein the carboxyl terminus of p75NTR-ECD was linked to the amino terminus of the Linker, and the gene fragment of the Linker was derived from the reverse primer (R3) sequence in the PCR reaction; the primer sequences (5'-3') of the PCR reaction are:

```
Forward primer F3 as shown in SEQ ID NO. 13:
CGCGGTACCATGGGTGCAGGGGCGACC
KpnI restriction site

Reverse primer R3 as shown in SEQ ID NO. 14:
GCTCCCACCTCCGCCTGAGCCCCCGCCACCGCTACCACCGCCCCCGTT

The nucleotide sequence of the Linker:
GTCTGTCGTCCCTCGTG.
```

(4) The carboxyl terminus of p75NTR-ECD-Linker was linked to the amino terminus of human IL-33 by an overlapping PCR reaction, wherein the p75NTR-ECD-Linker gene fragment contains a KpnI restriction site at the 5'-end and the IL-33 gene fragment contains a XbaI restriction site at the 3'-end. The primer sequences (5'-3') in the overlapping PCR reaction are:

```
Forward primer F4 (the same as the forward primer
F3 as shown in SEQ ID NO. 13):
CGCGGTACCATGGGTGCAGGGGCGACC
KpnI restriction site

Reverse primer R4 as shown in SEQ ID NO. 15:
CGCGGTACTAATTTTGTTAGTCGAATATTTCATTTTAGGTTTGCTCAGGC
3'-end sequence of the negative strand of IL-33
gene fragment

GGAGGTGGGAGC
5'-end sequence of the negative strand of p75NTR-
ECD-Linker gene fragment

Forward primer F5 as shown in SEQ ID NO. 16:
GCTCCCACCTCCGCCTGAGCAAACCTAAAATGAAATATTCGACTAACA
3'-end sequence of the positive strand of p75NTR-
ECD-Linker gene fragment
```

-continued

```
AAATTAGTACCGCG
5'-end sequence of the positive strand of IL-33
gene fragment

Reverse primer R5 as shown in SEQ ID NO. 17:
ACGTCTAGATTATGTCTCGGATAGCTTGAAGAGAATGTTTTCGG
XbaI restriction site
```

(5) The target product of the overlapping PCR (i.e., the gene fragment of fusion protein p75NTR-ECD-IL-33 containing a stop codon TAA at the terminus of IL-33 gene fragment) was enzymatically digested with KpnI and XbaI, and inserted into pcDNA3.1 (+) between the KpnI and XbaI restriction sites. The plasmids comprising the target gene of p75NTR-ECD-IL-33 was transformed in a host strain DH5a (supplied by ThermoFisher). The positive plasmids were extracted and sequenced for the inserted target gene to confirm the accuracy of the target gene sequence, and a recombinant plasmid (Vp75NTR-ECD-IL-33) comprising the target gene of p75NTR-ECD-IL-33 was obtained.

The recombinant plasmid (Vp75NTR-ECD-IL-33) can be used to prepare mRNAs and viral vectors that carry the target gene of p75NTR-ECD-IL-33. In a preferred embodiment, the recombinant plasmid Vp75NTR-ECD-IL-33 was linearized by a digestion with a single enzyme XbaI, DraII, ApaI, or PmeI. The mRNAs encoding p75NTR-ECD-IL-33 were obtained through the in vitro transcription by using a mRNA transcription kit (e.g mMESSAGE mMACHINE®T7 Transcription Kit, AM1344 from Ambion). The plasmid Vp75NTR-ECD-IL-33 can also be used to prepare viral vectors (comprising Lentivirus, adenovirus, adeno-associated virus, etc.) which express p75NTR-ECD-IL-33.

The present invention also provides a method for preparing a target protein which can be p75NTR-ECD (the extracellular domain of human p75NTR), human IL-33 or their fusion protein p5NTR-ECD-IL-33. In a preferred embodiment, the method for preparing the target protein comprises the following steps:

(1) Constructed and prepared the expression plasmids for producing p75NTR-ECD, IL-33 and p75NTR-ECD-IL-33: To facilitate the extraction and purification of target proteins, a Flag tag was linked to the amino terminus of p75NTR-ECD, IL-33 and p75NTR-ECD-IL-33 respectively (preferably, the Flag tag used in this example has an amino acid sequence as shown in SEQ ID NO. 18: AspTyrLysAspAspAspAspLys, and a nucleotide sequence as shown in SEQ ID NO. 19: GATTACAAAGATGACGATGATAAA; In other preferred embodiments, the Flag tag may have an amino acid sequence as shown in SEQ ID NO. 20: AspTyrLysAspHisAspGlyAspTyrLysAspHisAspIleAspTyrLysAspAspAs pAspLys, and a nucleotide sequence as shown in SEQ ID NO. 21: GACTACAAAGACCATGACGGTGATTATAAAGATCATGACATCGA CTACAAGGATGACGATGACAAG) to obtain Flag-tagged expression plasmids for preparing p75NTR-ECD (via PCR technology), IL-33 (via PCR technology) and p75NTR-ECD-IL-33 (via overlapping PCR technology): plasmid VFlag-p75NTR-ECD, plasmid VFlag-IL-33 and plasmid VFlag-p75NTR-ECD-IL-33 respectively; In other words, a Flag tag was linked to the amino end of the target protein by using the gene fragment of the target protein as template, a plasmid as vector and the two restriction sites as insertion sites of the target gene. If the target protein was p75NTR-ECD (p75NTR extracellular domain) or human IL-33, a regular PCR reaction was employed to obtain a expression plasmid for the Flag-tagged target protein: plasmid VFlag-p75NTR-ECD or plasmid VFlag-IL-33; If the target protein was the fusion protein p5NTR-ECD-IL-33, an overlapping PCR reaction was employed to obtain a expression plasmid for Flag-tagged p75NTR-ECD-IL-33: plasmid V Flag-p75NTR-ECD-IL-33. In this embodiment, pcDNA3.1(+) was selected as a vector, and KpnI and XbaI restriction sites were used as insertion sites as shown respectively:

a. A plasmid VFlag-p75NTR-ECD-IL-33 was prepared according to the method for constructing and preparing plasmid Vp75NTR-ECD-IL-33. The two forward primers were replaced:

```
The forward primer F1 used for cloning a p75NTR-
ECD gene fragment was replaced by F6 (as shown in
SEQ ID NO. 22):
ATGGATTACAAAGATGACGATGATAAAGGTGCAGGGGCGACCGGT
5'-end sequence of the positive chain of Flag tag

The forward primer F4 for the overlapping PCR was
replaced by F7 (as shown in SEQ ID NO. 23):
CGCGGTACCATGGATTACAAAGATGACGATGATAAAGGTGCAGG
KpnI restriction site Flag tag sequence
```

b. The primers used for preparing plasmid V Flag-p75NTR-ECD are as follows:

```
Forward primer F8 (as shown in SEQ ID NO. 24):
CGCGGTACCATGGATTACAAAGATGACGATGATAAAGGTGCAGGGGCGACC
KpnI restriction site Flag tag sequence

GGT
5'-end sequence of the positive chain of p75NTR-
ECD gene

Reverse primer R8 (as shown in SEQ ID NO. 25):
ACGTCTAGATTAGTTGTCTGTCGTCCCTCGTGTTACTACAG
XbaI restriction site
5'-end sequence of the negative chain of p75NTR-
ECD gene
```

c. PCR primers used for preparing plasmid V Flag-IL-33 are as follows:

```
Forward primer F9 (as shown in SEQ ID NO. 26):
CGCGGTACCATGGATTACAAAGATGACGATGATAAAAAACCTAAAATGAA
KpnI restriction site Flag tag sequence

ATATTCGACTAACAAAATTAGTACCGCG
5'-end sequence of the positive chain ofIL-33 gene

Reverse primer R9 (as shown in SEQ ID NO. 27):
ACGTCTAGATTATGTCTCGGATAGCTTGAAGAGAATGTTTTCGG
XbaI restriction site
5'-end sequence of the negative chain of IL-33 gene
```

(2) Transfected the expression plasmids into eukaryotic cells to obtain stable cell lines expressing target proteins. Preferably, mammalian cells were used. In this embodiment, HEK-293 cells were preferred.

HEK-293 cells were cultured with DMEM (Gibco) complete medium containing 10% (v/v) FBS (Gibco), 100 μg/ml penicillin and 100 μg/ml streptomycin and incubated in an incubator containing 5% (volume fraction) $CO_2$ at 37° C. When the cells grew to 80% confluency, they were subcultured. Before the transfection of plasmid, HEK-293 cells were seeded in 60-mm cell culture dish and cultured in DMEM (Gibco) medium containing 10% (v/v) FBS (Gibco). The next day, when the cells grew to 80% confluency, they were used for the plasmid transfection.

When transfected, 8.0 μg of plasmid VFlag-p75NTR-ECD, plasmid VFlag-IL-33 and plasmid VFlag-p75NTR-ECD-IL-33 was respectively diluted to 0.5 ml with Opti- MEM (Gibco) and gently stirred to prepare dilution A. 20 μl of Lipofectamine 2000 (Invitrogen) was diluted to 0.5 ml with Opti-MEM (Gibco) and gently stirred to prepare dilution B which was incubated at room temperature (20-25° C., the room temperature in this embodiment was 25° C., the same herein and after) for 5 minutes. The diluent A and B were mixed and stirred gently to form liposome transfection mixture which was kept at room temperature for 20 minutes. The liposome transfection mixture was added evenly into the culture medium in the 60-mm cell culture dish and blended gently. After 24 hours of continuous cell culture, the medium was replaced by DMEM (Gibco) screening medium containing 10% (v/v) FBS (Gibco), 100 μg/ml penicillin, 100 μg/ml streptomycin and 500 μg/ml neomycin sulfate (Clontech) to perform a screening culture. The screening medium was changed every 3 days, and the cells were passaged and subcultured every 6 days. After 3 weeks of culture, the cells were collected. Some of the cells were mixed in a complete medium containing 5% (v/v) dimethyl sulfoxide (Sigma-Aldrich) and preserved in liquid nitrogen as stable cell lines expressing p75NTR-ECD, IL-33 and p75NTR-ECD-IL-33: CLp75NTR-ECD, CL IL-33 and CLp75NTR-ECD-IL-33, respectively. The other cells were respectively used for the extraction and purification of target proteins p75NTR-ECD, IL-33 and p75NTR-ECD-IL-33.

(3) Extracted, preliminarily purified the target proteins and obtained the crude protein solutions. In this embodiment, the details were described below. The target proteins p75NTR-ECD, IL-33 and p75NTR-ECD-IL-33 were extracted and purified from the cells that stably expressed the target proteins by using the kit ANTI-FLAG® M2 Affinity Gel (Sigma-Aldrich, A2220) provided by Sigma-Aldrich to extract and purify Flag-labeled proteins. Operated according to the procedures of the product instruction. The collected cells were lysed with CelLytic M cell lysate (Sigma-Aldrich, C2978) containing 10 μl of protease inhibitor (Sigma-Aldrich, P8340) in 1 ml of lysate, and the supernatant was collected. An affinity chromatography column was prepared by filling the chromatography column with ANTI-FLAG M2 affinity resins, and the chromatography column was pre-equilibrated with an equilibrium solution. The supernatant was loaded onto the chromatography column, and the column was washed with 10-20 times column volume of TBS buffer (50 mM Tris HCl, with 150 mM NaCl, pH 7.4) to elute non-target proteins. The target protein was eluted with 0.1 M glycine hydrochloric acid solution with pH of 3.5 into a pre-frozen tube that was pre-loaded with 15-25 μl of 1 M Tris buffer with pH of 8.0 to obtain the crude solutions of p75NTR-ECD, IL-33 and p75NTR-ECD-IL-33 respectively.

A small amount of sample was taken to determine the protein concentration. The crude solutions of target proteins were directly used for further purification or stored in a freezer at −70° C.

(4) Removed Flag tag from the protein in the crude solution and obtained a purified target protein. In this embodiment, the details are described:

Flag tags at the amino terminus of amino terminal of target proteins p75NTR-ECD, IL-33 and p75NTR-ECD-IL-33 were removed by enzymatic digestions using recombinant bovine enterokinase (Sigma-Aldrich, E4906) provided by Sigma-Aldrich.

The crude solution of target protein was diluted to a concentration of 1.5 mg/ml to prepare the reaction solution by using a solution with 500 mM Tris-HCl, pH 8.0, 2.0 mM $CaCl_2$) and 1% (v/v) TWEEN20.

The enterokinase was added to the reaction solution at a rate of 0.02 unit per 1 mg fusion protein. The reaction solution was blended and kept at room temperature for 16 hours. After the reaction, the enterokinase was removed by using ENTEROKINASE REMOVAL KIT (Sigma-Aldrich, PRK-E) kit provided by Sigma-Aldrich to obtain the solutions of purified target proteins p75NTR-ECD, IL-33 and p75NTR-ECD-IL-33.

A small amount of sample was taken to determine the concentration and purity of protein. The solutions of purified target proteins were packed and frozen in a freezer at −70° C. or in liquid nitrogen.

I. Target Proteins were Identified:

1. Determination of the N-terminal amino acid sequence: target proteins p75NTR-ECD, IL-33 and p75NTR-ECD-IL-33 were transferred onto a PVDF membrane by SDS-PAGE electrophoresis, and the N-terminal amino acid sequences of the target proteins were determined by using a protein automatic sequencer Shimadzu PPSQ-31A.

The results showed that the N-terminal amino acid sequence of the target protein p75NTR-ECD was GlyAlaGlyAlaThrGlyArg, which was identical to the N-terminal amino acid sequence of the native protein of p75NTR-ECD. The N-terminal amino acid sequence of the target protein IL-33 was determined to be LysProLysMetLysTyrSer, which was identical to the N-terminal amino acid sequence of the native protein of IL-33. The N-terminal amino acid sequence of target protein p75NTR-ECD-IL-33 was identified to be GlyAlaGlyAlaThrGlyArg, which was identical to the N-terminal amino acid sequence of the fusion protein p75NTR-ECD-IL-33.

Figure 3:
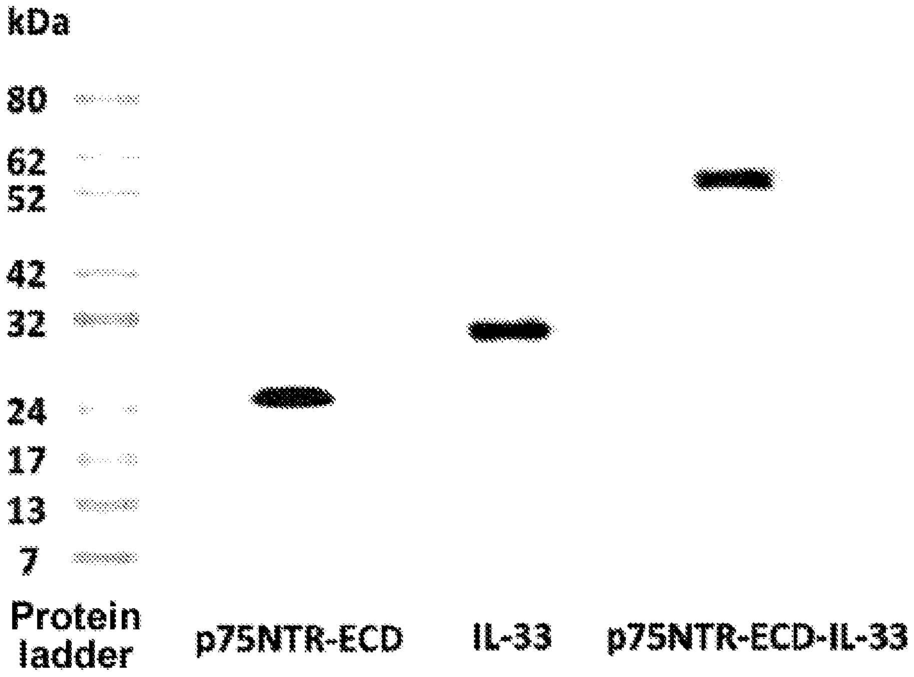
FIG. 3 is an electrophoresis pattern of fusion protein p75NTR-ECD-IL-33, protein p75NTR-ECD and protein IL-33 prepared in HEK-293 cells by SDS-PAGE immunoblotting assay in a specific embodiment of the present invention.

2. Western Blot Immunoassay: target proteins p75NTR-ECD, IL-33 and p75NTR-ECD-IL-33 were transferred onto a PVDF membrane via SDS-PAGE electrophoresis, and the immunoblotting identification was performed by using an Anti-p75 NGF Receptor antibody [NGFR5]-N-terminal (provided by Abcam, ab192774) that specifically recognizes p75NTR-ECD and an Anti-IL33 antibody (provided by Abcam, ab83873) that specifically recognizes IL-33. The results showed that the anti-p75 NGF Receptor antibody specifically recognized the target proteins p75NTR-ECD and p75NTR-ECD-IL-33, and the anti-IL33 antibody specifically recognized the target proteins IL-33 and p75NTR-ECD-IL-33. The results are shown in FIG. 3.

II. Assay on the In Vitro Stability of the Target Protein p75NTR-ECD-IL-33:

Differential scanning calorimetry (DSC) is a technique for directly identifying the stability of protein biomolecules in natural state. Protein biomolecules in solution maintain a balance between their natural (folding) and denatured (unfolding) conformations. The higher the midpoint of thermal transition (Tm), the more stable the molecules are.

The Tm values of target proteins p75NTR-ECD, IL-33 and p75NTR-ECD-IL-33 were determined by a differential scanning calorimeter MicroCal VP-Capillary DSC system.

Figure 4:
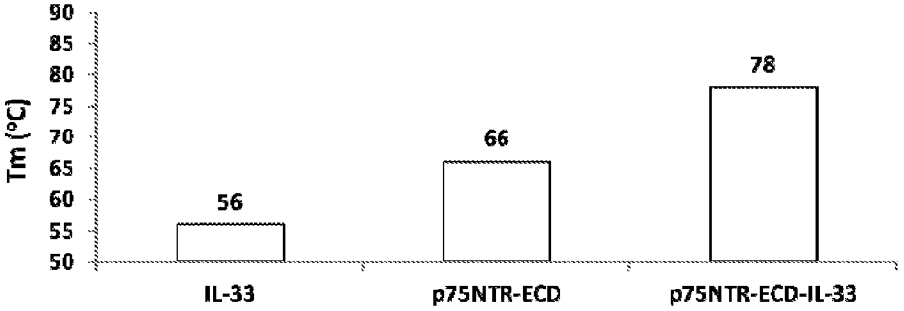
FIG. 4 is a schematic diagram showing the in vitro stability assay of fusion protein p75NTR-ECD-IL-33, protein p75NTR-ECD and IL-33 in a specific embodiment of the present invention.

It was determined that the Tm value of the target protein p75NTR-ECD-IL-33 was 78.0° C., the Tm value of the protein p75NTR-ECD was 66.0° C. and the Tm value of the protein IL-33 was 56.0° C. The results of the assay showed that the recombinant fusion protein p75NTR-ECD-IL-33 significantly improved the stability of proteins p75NTR-ECD and IL-33. The results were shown in FIG. 4.

III. Assay on the In Vivo Stability of the Target Protein p75NTR-ECD-IL-33:

The in vivo stability of target protein p75NTR-ECD-IL-33 was determined by measuring the half-life of the protein p75NTR-ECD-IL-33 in vivo. Twenty AD mice were separated equally to four groups: 5 mice in the control group, 5 mice in the p75NTR-ECD group (intraperitoneal injection with 300 ng p75NTR-ECD), 5 mice in the IL-33 group (intraperitoneal injection with 300 ng IL-33), and 5 mice in the p75NTR-ECD-IL-33 group (intraperitoneal injection with 300 ng p75NTR-ECD-IL-33). Venous blood was taken from tail vein at 2, 4, 6, 8, 12, 16, 20 and 24 hours after injection.

Figure 5:
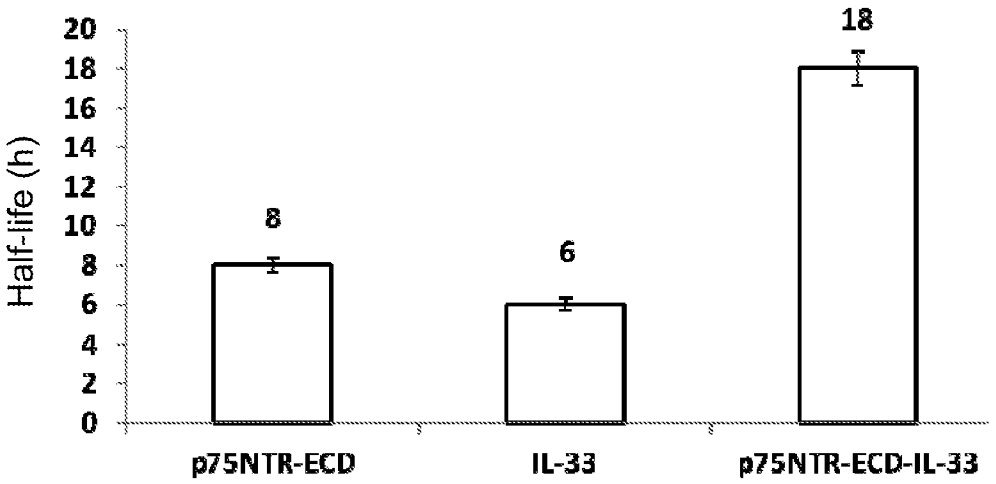
FIG. 5 is a schematic diagram showing the in vivo stability assay of fusion protein p75NTR-ECD-IL-33, protein p75NTR-ECD and IL-33 in a specific embodiment of the present invention.

The blood concentrations of p75NTR-ECD and p75NTR-ECD-IL-33 were determined by using the NGFR/p75ECD Rapid™ enzyme-linked immunosorbent assay (ELISA) Kit (Biosensis, BEK-2219-1P), and the blood concentrations of IL-33 and p75NTR-ECD-IL-33 were measured by using the Human IL-33 PicoKine™ ELISA Kit (Boster, EK0929). The half-lives of p75NTR-ECD, IL-33 and p75NTR-ECD-IL-33 were calculated. It was determined that the half-life of p75NTR-ECD was 8 hours, the half-life of IL-33 was 6 hours and the half-life of p75NTR-ECD-IL-33 was 18 hours. The results from the assay showed that the recombinant protein p75NTR-ECD-IL-33 significantly increased the stability of proteins p75NTR-ECD and IL-33 in vivo. The results were shown in FIG. 5.

IV. Determination of the Biological Activity of Target Protein p75NTR-ECD-IL-33 in the Prevention and Treatment of AD:

The determination of the in vivo biological activity of target protein p75NTR-ECD-IL-33 was performed by measuring the reduction in Aβ secretion and the degradation of Aβ that are promoted by the protein p75NTR-ECD-IL-33 in vivo. Twenty AD mice were separated equally to four groups: 5 mice in the control group, 5 mice in the p75NTR-ECD group (intraperitoneal injection with 300 ng p75NTR-ECD per day for 3 consecutive days), 5 mice in the IL-33 group (intraperitoneal injection with 300 ng p75NTR-ECD per day for 3 consecutive days), and 5 mice in the p75NTR-ECD-IL-33 group (intraperitoneal injection with 300 ng p75NTR-ECD per day for 3 consecutive days). The venous blood from the tails and the cerebral cortex were taken at 1 week after the injection. The cerebral cortex was frozen with dry ice, and homogenized with homogenate buffer containing protease inhibitor (250 mM sucrose, 20 mM pH 7.4 Tris-HCl, 1 mM EDTA and 1 mM EGTA) and Dunes homogenizer. The soluble Aβs were extracted with diethylamine.

Figure 6:
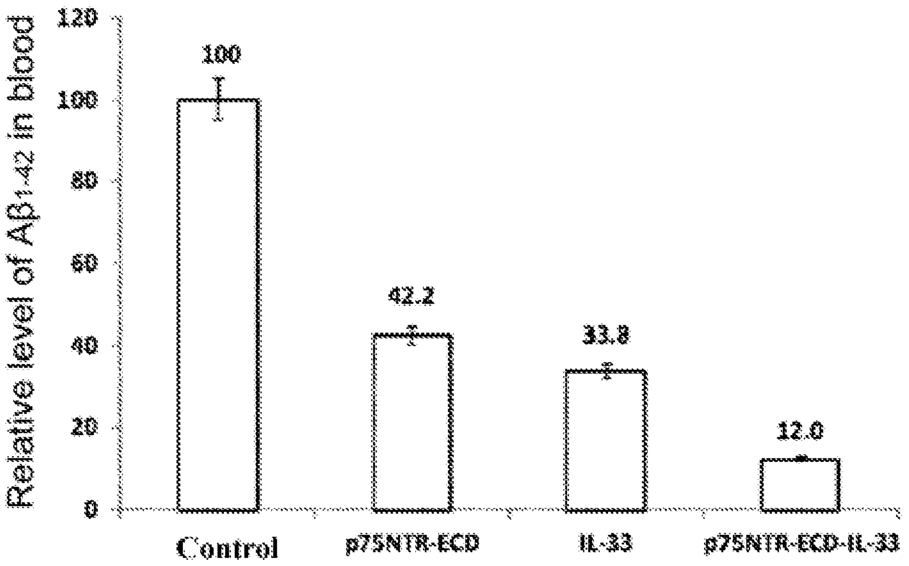
FIG. 6 is a diagram showing the changes in the concentrations of the Aβ1-42 in the blood of AD mice after the injection of fusion protein p75NTR-ECD-IL-33 in a specific embodiment of the present invention.
Figure 7:
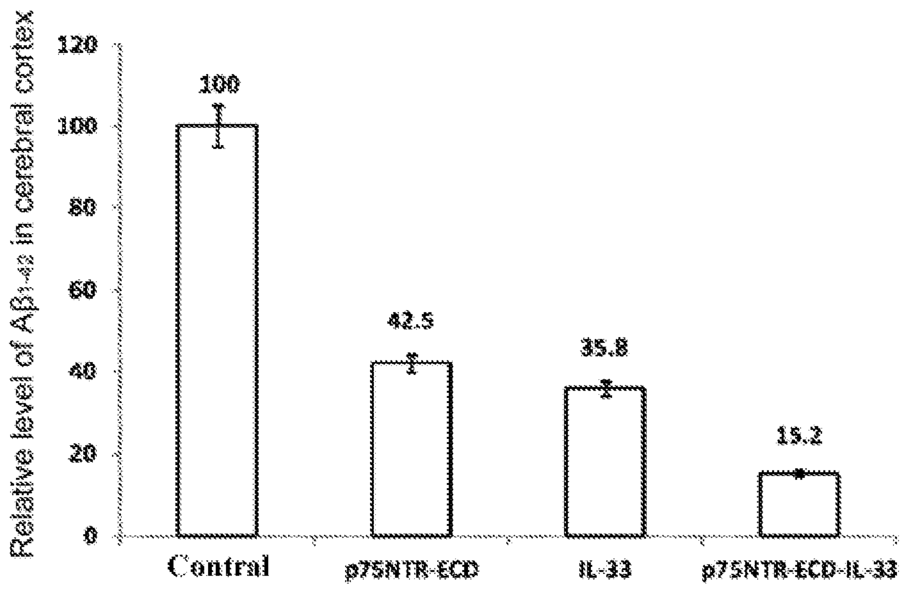
FIG. 7 is a diagram showing the changes in the contents of the Aβ1-42 in the cerebral cortex of AD mice after the injection of fusion protein p75NTR-ECD-IL-33 in a specific embodiment of the present invention.

The venous blood and soluble Aβ solution were employed to determine the Aβ1-42 content in the blood and the cerebral cortex by using an Amyloid beta 42 ELISA Kit, Mouse (Novex, KMB3441) supplied by Thermo Fisher. The results showed that compared with p75NTR-ECD and IL-33, the recombinant fusion protein p75NTR-ECD-IL-33 significantly promoted the degradation and removal of Aβ in vivo. After the fusion of p75NTR-ECD and IL-33, the recombinant fusion protein p75NTR-ECD-IL-33 significantly synergized and improved the biological functions of p75NTR-ECD and IL-33 in the prevention and treatment of AD. The results were shown in FIGS. 6 and 7.

The present invention also provides an application of the fusion protein described in the above embodiments in the preparation of medicines for preventing and treating Alzheimer's disease, and the medicaments for the prevention and treatment of Alzheimer's disease. The medicaments may be the fusion protein itself described in the above embodiments, or a mRNA liposome expressing the fusion protein, or a viral vector carrying a gene of the fusion protein. The administration methods of the medicaments in clinical use comprise: Fusion protein p75NTR-ECD-IL-33 can be injected directly into peritoneum, vein or brain; A mRNA liposome expressing fusion protein p75NTR-ECD-IL-33 can be applied intravenously or in brain; Viral vectors (comprising Lentivirus, adeno virus, adeno-associated virus etc.) carrying the gene of p75NTR-ECD-IL-33 can be applied intravenously or in brain.

Through the above experiments and measurements, the advantages of p75NTR-ECD-IL-33 obtained in the embodiments of the present invention comprise:

(1) The p75NTR-ECD-IL-33 has the biological functions of both p75NTR-ECD and IL-33. The p75NTR-ECD in the p75NTR-ECD-IL-33 binds to Aβ and its aggregates to prevent p75NTR from binding to Aβ and its aggregates and therefore protect central neurons from the neurotoxicity of Aβ. The IL-33 in the p75NTR-ECD-IL-33 induces the body to reduce the secretion of Aβ and promote the degradation of Aβ, and thus prevents the onset, the progression and the deterioration of AD. (2) The p75NTR-ECD-IL-33 is a fusion protein that can effectively enhance the stabilities of p75NTR-ECD and IL-33 and prolong their half-lives both in vitro and in vivo. (3) P75NTR-ECD-IL-33 can synergize the functions of p75NTR-ECD and IL-33 in the prevention and treatment of AD.

The p75NTR-ECD-IL-33 enables IL-33 to target Aβ precisely via the binding of p75NTR-ECD to Aβ, and induce the direct endocytosis of Aβ and its oligomers, or the secretion of enzymes to degrade Aβ, thereby improving the efficiency of the Aβ degradation. As a result, the biological activity of the fusion protein p75NTR-ECD-IL-33 is significantly increased compared with that of its monomers p75NTR-ECD and IL-33. (4) The P75NTR-ECD-IL-33 can be constructed to be expressed in eukaryotic cells and human body, so that p75NTR-ECD and IL-33 in p75NTR-ECD-IL-33 can be adequately glycosylated after translation, thus maintaining their native physical and chemical properties and biological functions under physiological conditions. (5) The p75NTR-ECD-IL-33 overcomes the shortcomings of the immunogenicity and the antibody-dependent cell-mediated cytotoxicity (ADCC) of the FC in p75NTR-ECD-FC so that the p75NTR-ECD-IL-33 is expected to become a safe and effective drug for the prevention and treatment of AD.

The contents described above are the further detailed descriptions of the present invention in connection with specific preferred embodiments, but the specific embodiments of the present invention are not just limited to these descriptions.

For the technicians in the technical field of the invention, without departing from the conception of the present invention, they can also make some equivalent substitutions or obvious variants that have the same functions or applications, however, all they make should be deemed to be in the protection scope of the invention.

The invention claimed is:

1. A pharmaceutical composition for binding and degrading amyloid beta-peptide (Aβ) in an Alzheimer's disease patient, comprising a p75NTR-ECD-IL-33 fusion protein and a pharmaceutically acceptable carrier;

wherein the fusion protein comprises, from amino terminus to carboxyl terminus:

a) an extracellular domain of human p75 neurotrophin receptor (p75NTR-ECD) consisting of the amino acid sequence of SEQ ID NO: 1, which is encoded by the nucleic acid sequence of SEQ ID NO: 2;

b) a flexible linker peptide consisting of the amino acid sequence of SEQ ID NO: 5, which is encoded by the nucleic acid sequence of SEO ID NO: 6; and c) a human interleukin-33 (IL-33) polypeptide consisting of the amino acid sequence of SEQ ID NO: 3, which is encoded by the nucleic acid sequence of SEQ ID NO: 4;

wherein the p75NTR-ECD-IL-33 fusion protein is encoded by the nucleic acid sequence of SEQ ID NO:8.

* * * * *